US007799366B2

(12) United States Patent
Kuiken et al.

(10) Patent No.: US 7,799,366 B2
(45) Date of Patent: Sep. 21, 2010

(54) METHOD FOR CREATING COVERS FOR PROSTHETIC DEVICES AND OTHER DYNAMIC SUPPORTING MEMBERS

(75) Inventors: Todd A. Kuiken, Oak Park, IL (US); Roger Good, Steamboat Springs, CO (US)

(73) Assignee: Rehabilitation Institute of Chicago, Chicago, IL (US)

( * ) Notice: Subject to any disclaimer, the term of this patent is extended or adjusted under 35 U.S.C. 154(b) by 1190 days.

(21) Appl. No.: 11/403,129

(22) Filed: Apr. 12, 2006

(65) Prior Publication Data

US 2006/0229755 A1  Oct. 12, 2006

Related U.S. Application Data

(60) Provisional application No. 60/670,561, filed on Apr. 12, 2005.

(51) Int. Cl.
*A61L 33/00* (2006.01)

(52) U.S. Cl. .................... 427/2.1; 264/40.1; 623/49; 427/2.31

(58) Field of Classification Search ............. 264/40.1; 623/49; 427/2.1, 2.31
See application file for complete search history.

(56) References Cited

U.S. PATENT DOCUMENTS

| 2,657,394 | A | 11/1953 | Milton, Jr. et al. |
| 2,684,487 | A | 7/1954 | Hansen et al. |
| 3,400,408 | A | 9/1968 | Garcia |
| 4,661,187 | A | 4/1987 | Beasley |
| 4,865,613 | A | 9/1989 | Rizzo |
| 4,929,213 | A | 5/1990 | Morgan |
| 4,990,162 | A | 2/1991 | LeBlanc et al. |
| 4,993,987 | A | 2/1991 | Hull et al. |
| 5,009,626 | A | 4/1991 | Katz |
| 5,085,665 | A | 2/1992 | Radocy et al. |
| 5,133,775 | A | 7/1992 | Chen |
| 5,152,800 | A | 10/1992 | Rothschild et al. |
| 5,280,305 | A | 1/1994 | Monroe et al. |
| 5,314,370 | A | 5/1994 | Flint |
| 5,363,159 | A | 11/1994 | Melvin |
| 5,376,127 | A | 12/1994 | Swanson |
| 5,647,147 | A | 7/1997 | Coomer |
| 5,709,954 | A | 1/1998 | Lyden et al. |
| 5,759,560 | A | 6/1998 | Dillon |
| 5,906,005 | A | 5/1999 | Niskala et al. |
| 5,980,475 | A | 11/1999 | Gibbons |
| 6,153,139 | A | 11/2000 | Marquette |

(Continued)

FOREIGN PATENT DOCUMENTS

GB  2 067 074 A  7/1981

*Primary Examiner*—Michael Barr
*Assistant Examiner*—Andrew Bowman
(74) *Attorney, Agent, or Firm*—Drinker Biddle & Reath LLP

(57) ABSTRACT

A unique flexible cover and a method are provided for creating such a flexible cover for a prosthesis, orthosis or other dynamic or flexible supporting device. One implementation of the method includes the steps of capturing an image of a target object comprising at least a portion of an existing body part of a person or another object, digitally processing and manipulating the image of the target object to form a representation, printing the representation onto a flexible cover, and applying the cover to a prosthesis, orthosis, or other object.

48 Claims, 11 Drawing Sheets

U.S. PATENT DOCUMENTS

| | | |
|---|---|---|
| 6,177,034 B1 * | 1/2001 | Ferrone .................. 264/40.1 |
| 6,498,961 B1 | 12/2002 | Hermet et al. |
| 6,549,819 B1 | 4/2003 | Danduran et al. |
| 6,597,965 B2 | 7/2003 | Graves et al. |
| 6,618,961 B1 | 9/2003 | Palau |
| 6,706,364 B2 | 3/2004 | Janusson et al. |
| 6,740,124 B1 | 5/2004 | Laghi |
| 6,829,377 B2 | 12/2004 | Milioto |
| 2004/0018881 A1 | 1/2004 | Hall |
| 2005/0015157 A1 * | 1/2005 | Doddroe et al. ............... 623/49 |
| 2005/0194106 A1 | 9/2005 | Scales |
| 2006/0000788 A1 | 1/2006 | Sholem |

* cited by examiner

METHOD FOR CREATING COVERS FOR PROSTHETIC DEVICES AND OTHER DYNAMIC SUPPORTING MEMBERS

CROSS-REFERENCE TO RELATED APPLICATIONS

This application claims the benefit of the filing date of U.S. Provisional Application No. 60/670,561, filed on Apr. 12, 2005, and incorporated by reference in its entirety.

TECHNICAL FIELD

This invention generally pertains to covers for prosthetic devices and other dynamic or flexible supporting devices. More particularly, this invention relates to covers for prosthetic or orthotic devices and other dynamic or flexible supporting members bearing photographic images of corresponding body parts or articles that give the covered devices the appearance of corresponding body parts or corresponding articles, both at rest and dynamically. The invention also relates to methods and apparatus for making such covers for prosthetic devices and other dynamic or flexible supporting devices that replicate the appearance of corresponding body parts or articles.

BACKGROUND

Amputees generally do not wish to draw attention to their prostheses. Accordingly, a good prosthesis should be as realistic looking and cosmetically appropriate as possible. While cosmetically appointed prostheses are commercially available, they typically exhibit limited realism. For example, one known prosthetic covering is a basic, monochromatic glove with indentations to resemble knuckles and nails. The glove comes in a limited selection of sizes (e.g., five sizes for adults and children) and colors (e.g., sixteen colors for each size). Unfortunately, it is not always possible to achieve a good color match between the cosmetic glove and the amputees' corresponding existing hand. Moreover, the glove is monochromatic and thus lacks a realistic depth of color. Finally, the glove often does not match the person's skin complexion (freckles, variations in skin tone, etc.)

One way to overcome these limitations has been to painstakingly paint detailed features onto a customized prosthetic or prosthetic cover (e.g., fingernails, toenails, skin creases, knuckle lines, hair, and base skin color). However, such customized prostheses are very costly due to the high artistic skill and substantial labor needed to make them. For example, an aesthetically enhanced hand cover marketed under the name LIVINGSKIN is available from Aesthetic Concerns of Middletown, N.Y. The material for the LIVINGSKIN cover is made up of three different layers, simulating the three layers of skin: epidermis, dermis and subcutaneous layers. Professional artists paint each individual cover to closely match the original limb, typically using photographs of the person's existing limb as a reference for color and detail. Although a prosthetic having such a cover can have a lifelike appearance, the required skill and labor to create the cover make handpainted prostheses or prosthesis covers too expensive for the average amputee. The costs will become all the more problematic when it becomes necessary to replace covers that become irreversibly soiled or damaged.

Thus, it can be seen that there is a need for improved aesthetically accurate covers for prostheses and orthoses that can be made by a cost-effective method and duplicated without excessive additional expense. There is also a need for improved, economical covers for prosthetic and orthotic devices and other dynamic or flexible supporting devices replicating the appearance of corresponding body parts or corresponding articles both at rest and dynamically. Finally, there is a need for a light chamber that makes it possible to produce photographic images of body parts with a degree of accuracy, realism and reproducibility sufficient to satisfy medical requirements, including the exacting requirements for making the covers of this invention.

SUMMARY

In accordance with the foregoing, a method and apparatus for creating a flexible cover for prostheses, orthoses and other dynamic or flexible supporting devices is provided. In one embodiment of the invention, the method includes the steps of capturing images of at least a portion of an existing body part of a person, digitally processing and manipulating the images as necessary, printing the resulting representation onto a flexible cover, and applying the cover to a prosthetic configured to replace a missing body part of a person or to an orthotic device designed to improve the function of movable body parts. The covers may also be supplied with appropriate images, and applied to dynamic or flexible devices like robotic arms or to other dynamic or flexible devices.

In a related embodiment of the invention, the capturing step includes inserting the body part of the person into a specially designed light chamber that enables the production of photographic images with a degree of accuracy, realism and reproducibility sufficient to satisfy the exacting requirements of the covers of this invention.

In one important embodiment, the chamber comprises an enclosure with at least one curved wall having at least three camera access holes with non-coplanar central axes, a source object access aperture for receiving body parts or articles to permit portions thereof to be photographed as desired, a color calibration scale, and one or more LED arrays to provide shadowless lighting of the source object.

In another embodiment, the image captured using a light chamber of the invention is one of a plurality of captured images of the body part, and the processing step includes merging a plurality of such captured images into a single two-dimensional representation of the body part. The processing step may further include enlarging or reducing the two-dimensional representation by a ratio sufficient to accommodate shrinkage or expansion of the cover that occurs during the applying step.

In yet another embodiment of the invention, the processing step further includes selecting a color profile that accounts for the hue of the material being used for the cover.

It is another object of the invention to permit a person to select from such varying images the skin color for a prosthetic cover that the person finds the most appealing.

In still another embodiment of the invention, the printing step includes putting the cover onto a substantially flat article, feeding the substantially flat article bearing the cover into a printer, and applying an image to the article.

In still another embodiment of the invention, the printing step includes putting the cover onto a substantially flat article, attaching the article to a substantially flat carrier, feeding the carrier with the attached article into a printer, and applying an image to the article.

In yet another embodiment, the cover is fed into a printer where a representation derived from the images of a source object is applied to the top surface of the cover and then it is flipped over and the feeding and printing steps are repeated.

Another embodiment of the invention is a method for creating a realistic looking cover configured to fit onto a prosthesis that includes the steps of placing an existing body part of a person into a light chamber comprising an enclosure that has a calibration reference scale contained within the enclosure; photographing the existing limb and the calibration reference scale within the light chamber; calibrating a printer using the calibration reference scale; and using the printer to print a representation of the existing body part onto a cover for the prosthesis.

In a related embodiment, the photographing step includes coupling a digital camera to an aperture in the enclosure described above and capturing an image of the existing limb through the aperture with the camera.

In another related embodiment, the calibrating step includes designing a specific International Color Consortium ("ICC") profile for the representation to be applied to the cover.

In still another embodiment, the printing step comprises fitting the cover over a transport form that is sized to stretch the cover so that it is enlarged from its nominal size to a size corresponding to the prosthesis that is to receive the cover, attaching the covered transport form to a carrier, and feeding the carrier into a printer to apply an image to the cover.

Yet another embodiment of the invention is a method for making a cover for a prosthesis or orthosis for a person that includes the steps of creating a cover that is configured to fit on the prosthesis or orthosis, fitting the cover onto a substantially flat article, attaching the article with the fitted cover to a substantially flat carrier, feeding the carrier with the attached article through a printer, and printing a representation of at least a part of the person's body onto the cover.

A further embodiment of the invention includes placing a part of a person's body corresponding to a missing limb into an enclosure, activating a light within the enclosure, digitally photographing the part from at least three different angles within the enclosure, creating a representation based on the visual data obtained in the photographing step, and applying the representation to a flexible cover for a prosthesis to replace the missing limb.

A further embodiment includes capturing a digital image of a body part, digitally processing and manipulating the digital image on a computer, and transferring the resulting representation from the computer to a printer to print the representation onto a cover for a prosthesis or an orthosis.

In yet another embodiment, the method further includes placing a heat-shrinkable cover replicating a body part prepared in accordance with the method of the invention onto a prosthesis or orthosis, and heating the cover to shrink it to produce a snug fit.

In still another related embodiment the method further includes stretching over a prosthetic or an orthotic cover replicating a body part prepared in accordance with the method of the invention.

In yet another related embodiment, the method further includes shifting the cover between printing onto the top and bottom surfaces of the cover by an amount sufficient to camouflage the interface between the top and bottom cover images.

In a further embodiment the method includes a differential stretch system to camouflage the interface between the top and bottom cover images in which in a first pass printing an image is applied to the top surface of an elastic cover maintained at a neutral stretch and then the cover is flipped 180° and an image is applied in a second pass printing while the printed side is maintained at an increased stretch and the exposed unprinted side is maintained at the neutral stretch.

In a further embodiment, the method includes editing the representation applied to the cover to remove scars, or other anomalies that would make both the healthy limb and the cosmetic covering look unrealistically symmetrical.

These and other aspects and attributes of embodiments of the invention will be described with reference to the accompanying drawings and detailed description of the invention.

DETAILED DESCRIPTION OF THE INVENTION

Figure 1A:
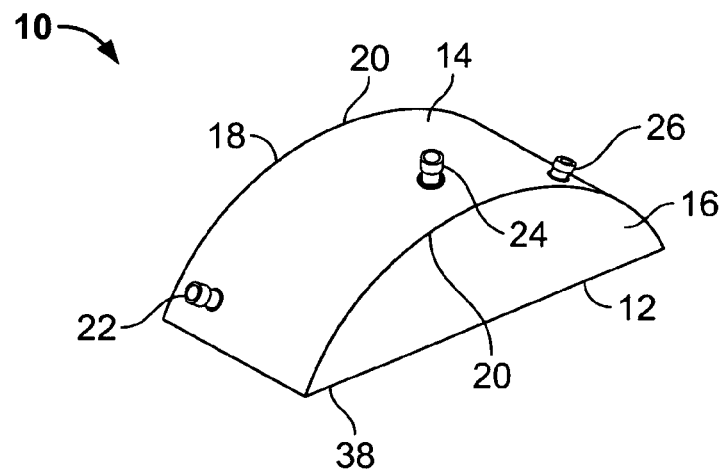
FIGS. 1A and 1B show a light chamber for photographing an existing limb or a supporting member under enhanced lighting conditions in accordance with embodiments of the invention.

Embodiments of the invention are generally directed to methods and apparatus for making covers for dynamic or flexible prosthetic and orthotic devices and other dynamic or flexible supporting devices and to the covers so produced. There are various ways of carrying out this method. In one embodiment, the method includes the following steps: (1) creating enhanced lighting conditions; (2) arranging one or more cameras to photograph from different vantage points a three-dimensional object comprising a body part, a body surface, or an article whose surface appearance is to be replicated on a prosthesis, orthosis or other dynamic supporting device (hereinafter referred to as the "source object"); (3) processing and manipulating the resulting images into a representation of the three-dimensional object for application to a flexible cover; (4) printing the representation onto a flexible cover configured to fit over and follow the contours of the prosthesis, orthosis or other supporting device (referred to below as the "target object"); and (6) securing the cover onto the surface of the target object.

Embodiments of the invention are illustrated below by describing methods and apparatus for making a prosthetic cover bearing a representation of a corresponding source object (body part). These examples are not to be construed as limiting the invention which relates not only to covers for prosthetic devices but also to covers for orthotic devices and to covers for other dynamic or flexible supporting members bearing representations of corresponding body parts or articles so that the covered devices have the appearance of corresponding body parts or corresponding articles, both at rest and dynamically. Thus, the target objects include prostheses, orthoses and other dynamic or flexible supporting members.

The Dynamic or Flexible Target Objects

The target objects onto which the covers of embodiments of the present invention are intended to be applied include prostheses for visible typically exposed dynamic or flexible body parts, particularly exposed tubular limb structures including hands, hands and arms up to the elbow, hands and arms up to the shoulder, fingers, feet, feet and ankles, feet and legs up to the knee, feet and legs up to the hip, as well as tubular sections of arms, legs, the neck or the trunk of the body. The target objects also include typically visible orthoses like leg and arm braces and other appliances used to support, align or improve the function of movable parts of the body. Finally, the covers may be used over any disfiguring scarring such as after-burn injuries or to simulate or hide body tattoos on the hands, arms, feet, legs, and trunk. The target objects do not include the face or the head.

Additionally, the covers may be supplied with appropriate images, and applied to dynamic or flexible devices like robotic arms or to other dynamic or flexible devices. For example, where it is desirable or necessary that a robotic arm supply not only a necessary function but also that it produce an anthropomorphic effect, the robotic arm may be supplied with a hand-wrist-arm cover bearing a human hand-wrist-arm image in accordance with this invention.

The Cover

Covers for use in embodiments of the invention are made of sheets of material that are configured to fit over and follow the contours of the target object. An example of a cover would be a blank glove 2 (i.e., the glove prior to the image of a person's hand being printed on it) as illustrated in FIG. 1A. The cover must have characteristics that are appropriate for the target object (e.g., elasticity and wear characteristics for a hand prosthesis cover). The material used for the cover preferably exhibits good wear resistance, moisture resistance, and ink retention characteristics. In one embodiment, the material has an ink receptor coating (as discussed below), to minimize color variation between different production runs of the cover. When a cover for a prosthesis is being created, it may be desirable to provide a variety of cover colors to facilitate matching of the final cover image to the person's skin color. In many applications, it is preferred that the cover be unitary or formed in one piece.

The cover material may be a heat-shrinkable material. Preferably, however, it will be an elastic material, that is, a flexible, low modulus of elasticity material, capable of expanding and contracting to return to its original or nominal dimensions without fatigue. Elastic materials that may be used in the practice of the invention include, but are not limited to, latex, silicone, rubber, and vinyl. Among these elastic materials, nitrile rubber (a co-polymer of butadiene and acrylonitrile) is currently preferred. If a heat-shrinkable material is used, it may be a shrinkable polymeric film such as heat-shrinkable polyvinyl chloride ("PVC"), polyethylene phthalate, and glycol modified polymers ("PETG") that have the requisite durability and shrink at a controllable uniform rate to produce a proper fit.

In certain applications such as a cover for a hand/arm prosthesis where one part of the prosthesis (e.g., the hand) is designed to rotate with respect to another part of the prosthesis (e.g., the arm), it may be desirable to use a multi-part cover, for example a cover where one part covers the hand and the other part covers the adjoining wrist and arm. In such a multi-part cover, at least two cover parts will abut and preferably overlap but remain free to move with respect to each other. Where the parts overlap, an appropriate lubricant may be applied to reduced friction and wear.

Additionally, where two or more parts of such a multi-part cover are intended to cover prosthesis components that are subject to different types or levels of wear, the cover parts may be made of different materials appropriate to the different wear levels. For example, in a hand-wrist-arm prosthesis, the cover for the hand component may be made of nitrile rubber while the cover for the wrist or arm component of the prosthesis may be made of vinyl. Furthermore, the thicknesses of the cover parts may also vary as desired to address the different requirements of the prosthesis components. In all cases following the process explained in more detail below, embodiments of the present invention make it possible to produce consistent images across the cover parts notwithstanding variations in the printing characteristics or color (or differences in the ICC profile) of the material used to make the cover parts.

As noted above, the cover may be used with burn victims as itself a skin prosthesis" applied after healing at the burn site.

The cover material may be any appropriate color or shade, and it may be opaque or translucent. Indeed, in some applications it may be desirable to use a transparent material and to modify the image processing and modifying step to produce an appropriate image for inside-the-cover printing. In this case an additional step would be performed after the printing is completed in which the cover is turned inside-out after printing to place the image in a protected location on the inside of the cover and therefore behind the exposed surface of the cover.

The cover material may be coated with an acrylic acetate to facilitate reliable and consistent color reproduction in the final product. If an acrylic acetate coating is used, then the coating should be applied using rollers, wire form coating, or other application method that produces a uniform and smooth coating to help insure an accurate and reproducible color profile in the final cover image. Among the above coating methods, wire form coating is currently preferred. Following coating, the cover surface should be allowed to cure before an image is printed on it, preferably using an inkjet printer as discussed below. Although the acrylic acetate can be applied to the cover material before the covers are made, it is preferred to apply it to formed covers to insure precise and uniform coating.

The cover will be shaped to fit over the dynamic or flexible target object (e.g., a glove over a hand prosthesis) either by way of an undersize or stretch fit for a cover made of an elastic material or by way of an oversize fit for a cover made of a heat shrinkable material. Where the target object is a prosthetic hand, for example, the cover should be shaped as a glove optionally including wrist and arm portions, optionally including independently movable cover parts as discussed earlier. Where an elastic material is used it should have elasticity characteristics that permit it to be stretched without damage to at least about 25% of its nominal size and preferably to about 10% of its nominal size. This will ensure that a close-fitting cover can be made that once placed on the dynamic or flexible target object will tightly and closely follow the target object contours, fitting into the nooks and crannies of the target object to the extent reasonably possible and staying there as the target object moves and flexes.

The thickness of the cover material should be sufficient to make it durable, but it must also be thin enough to enable it to follow the contours of the target object. Generally, the material should be from about 0.003 to about 0.050 inches in thickness and more preferably it will be from about 0.008 to about 0.012 inches in thickness.

The surface of the cover may be smooth. Alternatively it may be provided with a roughened or enhanced friction surface or with roughened or enhanced friction portions in selected areas of the cover. For example, the finger tips of a hand prosthesis cover or the heel of a foot prosthesis cover may be provided with roughened or enhanced friction portions. Gripping or other areas that are subject to increased wear may also be reinforced by placing additional material thickness at these areas of the cover. Finally, the cover may be provided with a textured surface emulating the tactile characteristics of the surface of the limb replaced by the prosthesis. For example, a cover for a hand prosthesis with such a surface would give the person fitted with a touch-sensitive hand prosthesis more accurate feedback from the prosthetic hand. It would also give others who touch the textured surface of the hand prosthesis cover tactile feedback making the prosthetic hand seem more lifelike to them.

In one alternative embodiment, a two-layer cover may be used. In this embodiment, the inner cover portion would provide the physical texture of the prosthesis, including fingernail beds, the palm creases, etc. One method of making such an inner cover is described in U.S. Pat. No. 2,453,604 in connection with forming a mold that is the reversed replica of a human hand and using that mold to make elastic gloves that replicate the contours of a human hand. In this embodiment of the present invention, a generally smooth outer cover portion bearing the representation of the human hand (or other limb) would be fit over the inner cover.

Additionally, elastic gloves for prostheses that replicate the contours of a human hand (e.g. those made by processes like that of U.S. Pat. No. 2,453,604 referred to above) may be flattened and printed with the representation of the corresponding limb in accordance with the process of the present invention.

The Light Chamber

Figure 1B:
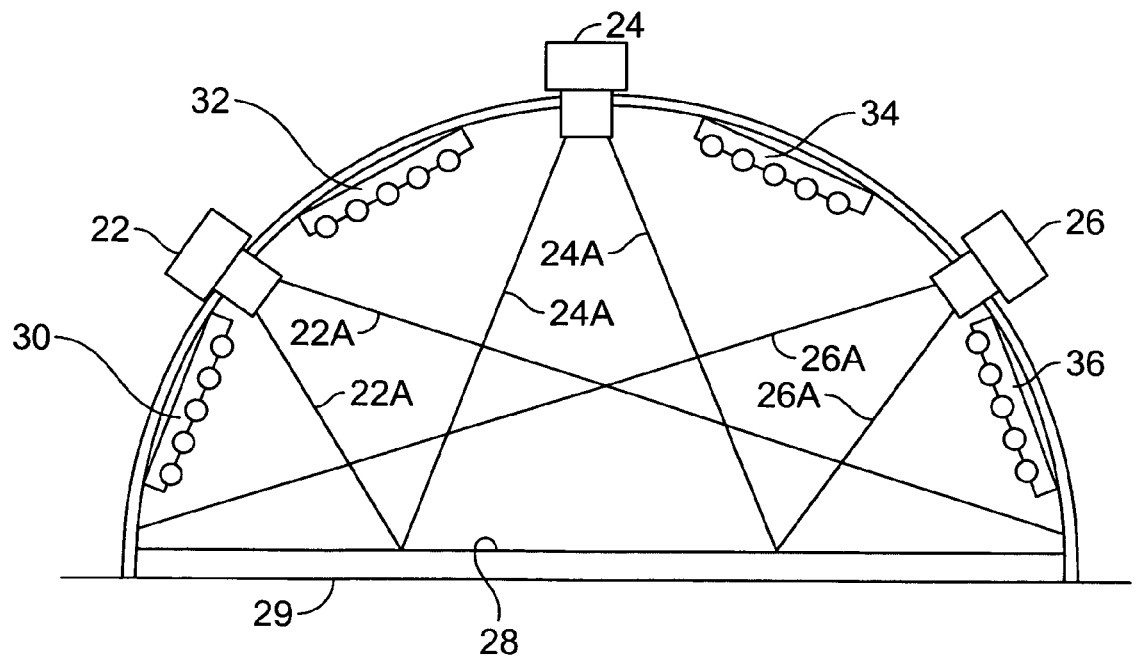

It is preferred in the practice of the present invention that a light chamber providing enhanced lighting conditions be used to produce the photographic images that are to be used in creating the representation transferred onto the cover. One such enhanced light chamber 10 is illustrated in FIGS. 1A and 1B. Although the inventive aspects of the chamber do not reside in its dimensions, in one preferred embodiment the light chamber may 40-48 inches wide by 24-30 inches tall. As shown in these figures, chamber 10 comprises an enclosed generally hemispherical shape with a generally flat base 12, a generally curved top 14, a generally flat access end 16 and a generally flat back end 18 onto which the object to be photographed will usually rest. The chamber may be constructed of rigid material such as generally rigid plastic, metal, or other appropriate material. Alternatively, the chamber may include a rigid framework 20 corresponding generally to the outline of chamber 10 in FIG. 1A, covered by a flexible fabric. The framework may be made of plastic, aluminum or other appropriate rigid material in the form of bars, strips or tubes. The framework may be fixed in place or it may be adapted to be folded for storage when not in use. Finally, the flexible fabric may be permanently attached to the framework or it may be removably attached, for example, by Velcro or snap fasteners. The inner surface of the chamber preferably is coated or lined to produce a reflective surface comparable to the silver or white reflective surfaces of reflective photographic umbrellas. It is preferred that the inner surface have a silver reflective surface.

Access end 16 of chamber 10 may be entirely open for receiving the body parts or articles that are to be photographed or it may be closed and provided with an access aperture (not shown) for receiving the body parts (e.g. a hand and wrist inside the chamber with the arm extending outside). This opening may be provided with a curtain or tarp (not shown) to block out extraneous light. If an access aperture is provided as discussed above, a sleeve (not shown) may encircle the aperture to block out extraneous light.

Back end 18 of the chamber preferably is open to permit a limb to extend out from the back of the chamber if necessary. For example, where it is necessary to photograph a person's forearm, the area of the forearm to be photographed will be properly positioned within the chamber with the hand extending through the back end of the chamber. In an alternate embodiment, the back end may be covered and an egress aperture (with or without a sleeve) provided to permit the limb to extend through the back of the chamber.

It is preferred at least three camera mount apertures 22, 24, and 26 as shown are formed in curved top 14 permitting the contents of the chamber to be photographed from varying angles. It is preferred that the central axes of these camera mount apertures not be coplanar to ensure the production of optimal three-dimensional images from the photographic images taken of a particular source object in the chamber. Also, any desired number of camera mount apertures may be formed in curved top 14. The camera mount openings may be provided with sleeves (not shown) to hold the camera(s) in place during the image-taking process. Preferably, these sleeves will be attached to framework 20. Also, the cameras may be supported independently of the camera mount apertures by, for example, supporting the camera(s) on tripod(s). The image coverage by cameras mounted to the chamber are represented by lines 22A, 24A and 26A which illustrate the field of view of the cameras.

Light chamber 10 preferably will include a calibrated scale 28 positioned on the bottom 29 of the chamber to assist in assessing color in the final image applied to the cover. The scale may be a checkerboard pattern with two inch square calibrated three-step gray scale patches. Alternatively, a color scale could be used such as a Greta Macbeth color chart.

RGB Values for gray scale patches preferably will be "255, 255, 255" for white, "128, 128, 128" for the mid tone, and "0, 0, 0" for black. In another embodiment, only the outer perimeter of the inner surface of the light tent will have this checkerboard pattern, and the center portion will be a neutral gray (RGB "128, 128, 128"). The checkerboard pattern may also have lines at predetermined increments (e.g., 0.1 inch) to provide size scale reference information. For example, if a hand is the source object being photographed, this size scale information can be used to compute the diameter of the fingers, wrist, palm, etc. Since digital cameras derive color via gray scale ratios as measured through red green and blue filters, at the production phase the calibrated gray scale can be used to remove any color cast from the photographic reproduction of the scale in the background thereby insuring the color of the skin will be accurately represented.

LED arrays 30, 32, 34, and 36 are provided at a fixed distance from the imaging area to light the source object. The LED arrays are of a fixed intensity and provide uniform lighting that shadowlessly lights the entire object including its crevices and grooves to produce optimal images. While four arrays are shown in FIG. 1B, any appropriate number of arrays may be used. The use of LED arrays as the light source in the light chamber is preferred, although other less preferred light sources also could be used.

The LED arrays preferably will be selected to provide a color temperature between about 5000 and 5700 degrees K. This color temperature represents the most common daylight color temperature, and is the most pleasing to normal viewing. LED arrays do not generate significant amounts of heat, thereby ensuring that if a person were to touch them while a limb is being photographed within the chamber, there is no risk of burn injuries. Also, LED's operate on low voltage, eliminating risks associated with locating high voltage near the limb. Furthermore, single LED failures in the array do not compromise the quality of the image, where if more conventional lighting were used, single failures could adversely affect the final image. Finally, once the light chamber is arranged, there is no further need for calibration or set up on the part of the technician to capture the images as needed.

Since a person's good limb is in fact living tissue, the color of the skin on the living limb goes through numerous changes over the course of a day due to changes in the skin's perfusion of blood associated with, among other things, varying physical orientation of the limb. This variation in skin color can be reproduced by photographing the limb in different physical orientations. For example, the chamber may be mounted for pivotal movement along edge 38, so that photographs of a particular good limb can be taken in a generally resting horizontal position, an upwardly angled (for example, 30° above the horizontal) position or a downwardly angled position (for example, 30° below the horizontal. Since the limb color will vary with the varying blood perfusion associated with these different positions, the color of the limb in these photographs will vary to correspond to the level of profusion.

Changes in skin perfusion are also associated with changes in temperature. The light chamber therefore may also be equipped to reproduce variations in skin color by providing means to heat or cool the chamber to produce such changes in surface perfusion in the limb being photographed associated with changes in temperature. To do this, it is preferred that the access and back ends of the chamber be closed and provided with access and egress apertures (preferably with sleeves) as discussed above. Heating and cooling will be supplied to the chamber by conventional means.

Varying the level of skin perfusion leads into yet another aspect of the present invention. Thus, images reflecting differing skin perfusion may be generated for a particular limb that is to serve as a source object for a prosthesis cover. The person choosing the final image to be applied to the cover can choose the optimum image from these differing images thereby maximizing the satisfaction of the person receiving the final prosthesis cover. For example, images may be taken with the limb at different temperatures and thus different skin perfusion and different coloring (e.g. a warmer hand may be more red in color and a colder hand may be more blue). A sample of these different images can be printed and the person receiving the prosthetic covering can choose which of the samples they prefer be used to make the final cosmetic glove. Also, if the person receiving the prosthetic covering wants to alter these images, for example by enhancing the red component to suggest a warmer limb, the image can be easily so altered at this point and printed for approval.

Figure 2:
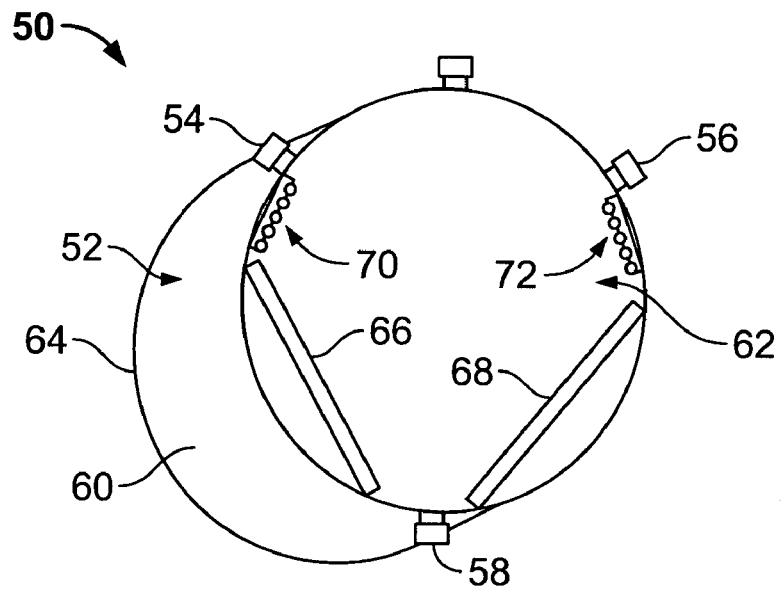
FIG. 2 shows an alternate light chamber design for photographing an existing limb or a supporting member under enhanced lighting conditions in accordance with embodiments of the invention.

Another embodiment of a light chamber 50 in accordance with the present invention is shown in FIG. 2. This light chamber has a generally cylindrical housing 52 and camera access apertures 54, 56 and 58. As shown, the chamber includes a cylindrical wall 60, an access end 62 and a base 64. The cylindrical chamber is preferably coated or lined on its interior surface as described above with respect to clamber 10. Also, as described above with respect to chamber 10, chamber 50 will be provided with calibrated scales 66 and 68 and LED arrays 70 and 72.

The above light chambers may be used for applications outside of preparation of covers in accordance with embodiments of the present invention to reproduce very accurate matches of skin tone and also depth and overall image for a variety of other purposes. For example, the light chamber may be used in skin mapping, for documentation of accurate body part images, and for pre-implant surgical applications where it is important to obtain the precise color for an implant.

The Printing Equipment

The method described herein may be carried out using a conventional personal computer and conventional printer that are hard-wired or wirelessly linked to one another. The printer should be capable of responding to digital color profiles and of printing on materials up to about 0.060 inches in thickness. One printer that has been found to be particularly useful in the practice of the present invention is the Epson 4800 printer, available from Seiko Epson Corporation of Japan. Also, the ink used, which may be pigment or dye-based, must have good water-resistance, color consistency, color stability, durability. Epson K3 inks are currently preferred.

Since different types and colors of base cover material respond to printed images differently, it is desirable to have predetermined calibration data for each contemplated type of base cover material. For example, a custom ICC profile may be created for each color and type of cover material. Such profiles can be generated by printing known color values on the cover material, allowing the colors on the material to stabilize for a period of time, and measuring the resulting color characteristics. Ink ratios can be adjusted and recorded through incremental testing until the printed characteristics are suitably close to the calibrated target. If the cover material is transparent or translucent, the color of the target object (e.g., the color of a covered prosthetic limb) will be taken into account during the calibration process. If ICC profiles are used, then the camera, printer, image manipulation software, and computer monitor preferably will all be capable of being calibrated using the ICC profiles.

Method steps that may be employed in a preferred embodiment of the invention will now be described in detail. It is to be understood, however, that there are many possible ways to carry out each of these steps, and that the ways described below are only examples.

Creating Enhanced Lighting Conditions

The first step of creating optimal lighting conditions is carried out by setting up a light chamber, such as the light chamber 10 of FIGS. 1A & 1B or the light chamber of FIG. 2. It is greatly preferred that shadows, be eliminated to avoid distorting the color accuracy of the image. It is also preferred that a fixed lighting set-up be arranged (i.e. the set ups of FIGS. 1A & 1B or of FIG. 2) to eliminate inconsistencies that would arise if a new set-up were arranged for each source object. Of course, less desirable lighting approaches may be used if necessary.

It is preferred that light chamber 10 be used so as to facilitate accurate reproduction of colors and features of the three-dimensional object without undesired shadowing effects as discussed above. In one suitable configuration, four high-intensity fixed position LED arrays with a color temperature of 5000K-5700K are positioned within light chamber 10 around the source object. An LED array capable of being triggered via wireless synchronization from a camera can be used if desired. Size and color scale tools also set up within the light chamber also as described earlier.

Camera Set-Up

The step of setting up one or more cameras near the source object according to an embodiment of the invention will now be described. In this embodiment, a digital camera is physically positioned near the object and set to a resolution and image size that is high enough to confer an acceptable level of detail. One possible advantage of a digital camera over a film camera is that digital photographs allow for better color correction and color matching under varying lighting conditions. The appropriate resolution and image size settings for the camera may be determined based on fine art photography techniques. For example, if the aesthetic covering needs to look realistic when viewed from a distance greater than 12 inches, then each camera should capture at least 240 pixels for each inch of printed image.

For example, if a three-dimensional object that is to be photographed is an amputee's existing hand, and the aesthetic covering to be produced is a glove for a prosthetic hand intended to appear life-like when viewed from a distance greater than 12 inches, and if the glove has a length of about 17 inches from the fingertip to the bottom of the glove (near the elbow) and has a width of about 7 inches, then a suggested resolution of each camera would be as follows:

17 inches×240 pixels per inch=4080 pixels 7 inches×240 pixels per inch=1680 pixels Because current digital cameras often have a 3:2 aspect ratio for image capture, the camera in this example may be set to a resolution of at least 4080×2720 (11.1 megapixels) prior to photographing the amputee's existing hand. Additionally, it is preferred that the camera be set to capture and store images in an uncompressed or "RAW" format, although JPG or similar formats can be used. Given that the process for matching color of living skin, and that image capture will be done by different technicians, different locations, RAW images are preferred because variation in camera software will not affect the results ultimately obtained in the processing of the RAW data.

Thus, where a cover is designed to be stretched 10% beyond the cover size when it is later fitted over the prosthesis (the "target size"), the image as photographed can be manipulated to achieve the desired quality in the final image on the cover. In order to do this in this 10% stretch example, the source object image is enlarged 10% beyond the target size. Thus, when the glove is fitted onto the prosthesis it is reduced 10% and therefore carries the source object image as photographed (as processed and manipulated).

Capturing a Representation of the Source Object

According to an embodiment of the invention, photographs of the source object are taken from various camera mount apertures around the center of the light chamber to capture a complete view. For example, these images may be taken from 30, 45, 90, 135 and 150 degree angles (which would require two additional apertures like features 22, 24, and 26 of FIGS. 1A-1B). However, embodiments of the invention can be carried out using any number of camera angles and images, depending on the particular application and desired cost. In order to correctly capture an accurate three-dimensional image, it is also desirable that the cameras be positioned at angles other than 90 degrees to the subject in order to ensure proper depth rendering. Ideally, the angles at which the photographs are taken will be chosen to ensure at least about 10% overlap and preferably at least about 30% overlap between the images. The size and color scale tools contained within the light chamber are captured in photographs for reference later for matching the processed and printed representation to the characteristics of the three-dimensional object. Finally, it is desirable that perspective control lenses be used to eliminate the distortion that may occur in two-dimensional representations of images that have a deep depth of field.

To photograph a person's existing limb, for example, the person inserts the limb (e.g., a hand), through access aperture 20 of light chamber 10 of FIGS. 1A and 1B. Then, photographs of the hand are taken by triggering the cameras and the LED arrays either remotely or directly. The photographs may be taken from selected angles to facilitate accurate reproduction of the major visible areas of the hand. For example, three photographs taken at 60, 90 and 120 degrees for the back of the hand and a single photograph at 90 degrees from the front (using chamber 50) of the hand may be sufficient. These images will ultimately be printed on opposite sides of a glove-shaped base cover during the printing step, which is described below in more detail.

This example assumes, however, that the amputee has an existing corresponding limb to serve as a model for photographic replication. For situations where a person has no suitable corresponding limb, such as a double amputee, a selected standard image or a photograph of a model's limb having suitable physical characteristics may be used. A library of images of limbs may be generated for this purpose, so that amputees may choose a desired image from the library for application to a prosthesis cover in accordance with the invention.

The invention provides other ways of addressing occasions where it is necessary or desirable to generate color profiles and other visual characteristics from body parts or areas other than corresponding body parts. For example, in a case of a bilateral hand amputee or a burn victim, another body area having corresponding visual characteristics could be scanned to obtain the appropriate color profile for the cover. Thus, this image could be processed and manipulated in accordance with embodiments of the invention (e.g. by using the "clone" and "patch" features of PhotoShop) to produce an image suitable for application to the cover.

Processing the Digital Images into a Representation of the Source Object

In an embodiment of the invention, processing the digital images to form the representation of the source object, includes adjusting the representation if necessary to achieve the appropriate color, and resizing the representation, if necessary to accommodate expansion or contraction that is anticipated to occur when the cover to which the representation is applied is fitted onto a three-dimensional object. The process of converting multiple images of the three dimensional object into the representation consists of stitching together the various images that form a 180 degree view of the object to form a flat image of the appropriate dimensions. In this process, the various sections are precisely matched to various skin features and markings to ensure proper image alignment. The final two-dimensional representation is then flipped if necessary and sized to the correct two-dimensional size to match the dimensions of the prosthesis on which the cover will be worn on. Also, the representation may be edited as desired including editing to remove scars or other anomalies that would make both the healthy limb and the covered prosthetic look unrealistically symmetrical.

More specifically, the captured digital images may be merged or digitally "stitched" into a two-dimensional representation to be used in the printing process. The merging process can be performed using imaging processing software that has photo merge capability and ICC profile management capabilities. An Adobe Photoshop program photo merge feature may be used for this purpose. The photo merge process allows the multiple images to be merged together seamlessly into a two dimensional representation to be printed on the cover. Adobe Photoshop version CS2 is currently preferred. Also, where the target object is generally a mirror image of the prosthesis, the "flip invert" or "invert" features of the software can be used to convert the representation as required for the cover of the prosthetic Once the flattened representation of the three-dimensional object is created and appropriate sized, the desired color may be matched and calibrated. A reference gray scale contained within the light chamber (and therefore captured in the image along with the three-dimensional object) may be used for this purpose. For example, digital cameras typically capture images as a combination of gray scale representations of red, green and blue color channels. Accordingly, the three checkerboard colors of RGB can be set to exact values, facilitating a nearly perfect color rendition of anything in the light chamber. Preferably, the computer monitor used in setting up the final printing colors is also calibrated with an ICC profile.

Printing the Representation onto a Flexible Cover

To print the two-dimensional representation onto a flexible cover in an embodiment of the invention, the base cover is first placed on a transport form. The transport form should be substantially flat and rigid to help hold the cover in a desired two-dimensional shape during printing. As explained earlier, it is desirable to print the representation such that it has the desired size and color characteristics of the target object. One way to accomplish this is to stretch the material over the transport form by an amount equaling the degree of stretch required for the target fit. The transport form may be sized to yield the desired amount of stretch.

Figure 3:
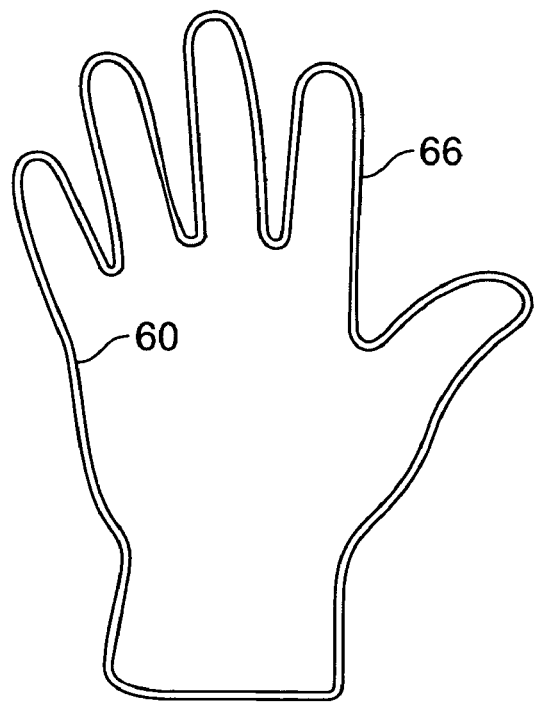
FIG. 3 shows a base cover fitted over a transport form in an embodiment of the invention.
Figure 4:
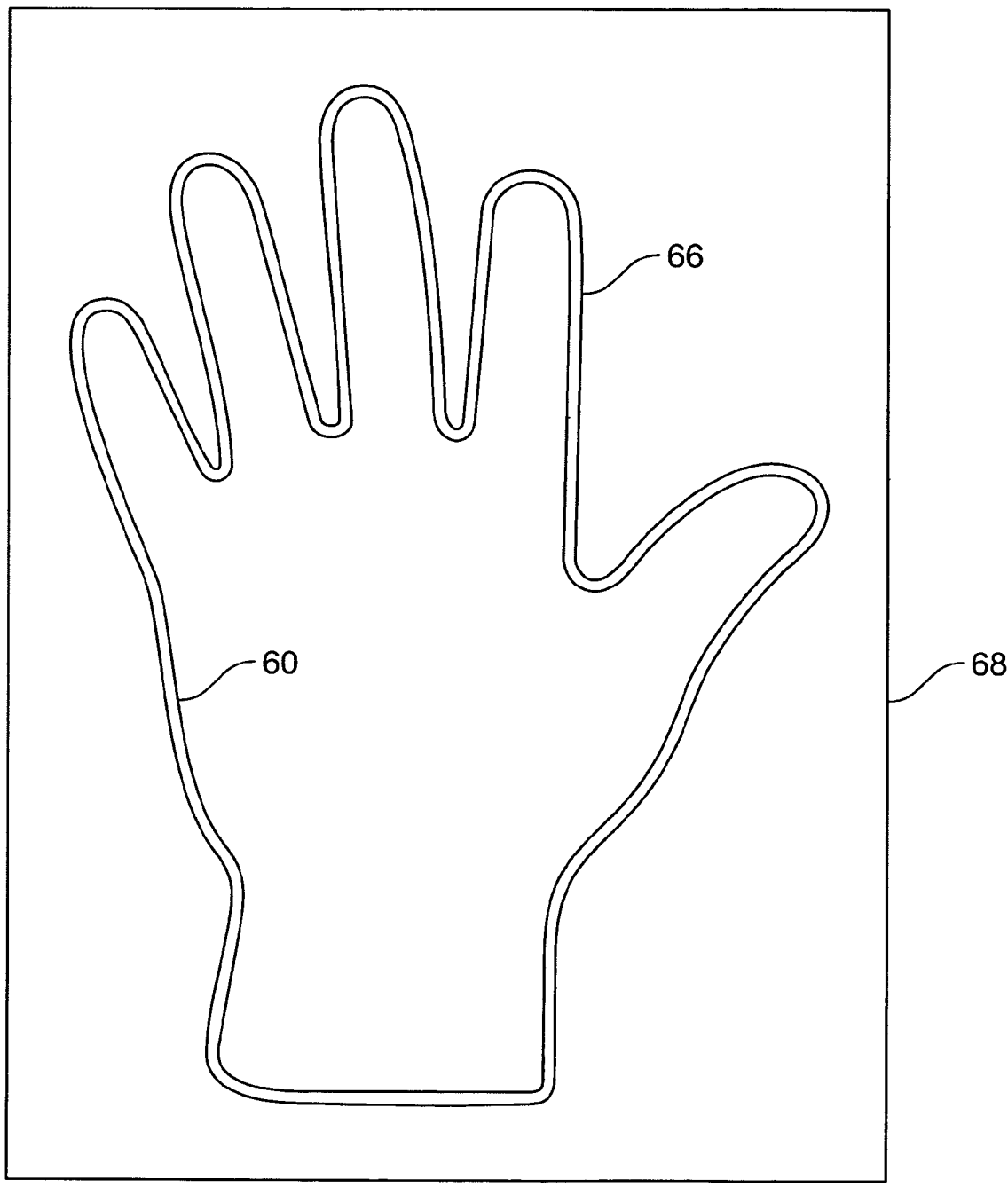
FIG. 4 shows a transport form having a base cover fitted thereon, with the transport form being attached to a carrier in an embodiment of the invention.

Referring to FIGS. 3, and 4, an example of how a cover is placed on a transport form and attached to a carrier will now be described. In this example, the cover is an elastic glove that is shaped to fit onto a prosthetic hand. The transport form 60 is hand-shaped. The shape and size of the transport form 60 is designed to provide the desired degree of stretch to the elastic glove during printing.

Referring to FIG. 3 the cover 66 (i.e., the elastic glove), is fitted over the transport form 60 in preparation for printing. (The thickness of the cover is exaggerated for purposes of illustration.) The transport form with the cover on it is then placed on an alignment carrier 68, as shown in FIG. 4, to properly register the position for printing. In this process, the glove form size may be predefined to various standard glove sizes. The glove form is then positioned on a specifically positioned registration guide to insure the image is printed in the correct location on the glove. The alignment carrier may be designed to transport multiple gloves at a time through the printer, to ensure consistency between gloves. In one embodiment, the transport form 60 stretches the base cover to 105% of its final installed surface area. Accordingly, the two dimensional representation is printed in 105% of its nominal size, corresponding to the size of the stretched glove. Using a single-sided printer, once the glove had been printed on one side, the transport form 60 is flipped over to print the other side. The glove and transport are then inserted into a carrier that is used to position and print the opposite side of the glove and the opposite side is printed.

One possible approach to ensuring proper registration involves taking a photograph of a blank cover mounted appropriately on the transport mechanism which will be, for example, an 8½×11 sheet which will accurately and repeatably move through the printer. This photograph can then be displayed on the computer monitor where the printed representation will be moved into position to precisely print onto the blank cover image to ensure proper and accurate registration in the final printed cover.

It is also highly desirable to eliminate or minimize unprinted seams between the top and the bottom images. This can be accomplished generally by techniques by which the representation on the opposite sides of the cover overlap along the interface of the top and bottom cover images. Typically, the overlapping areas will be printed at a reduced opacity level where the overlap occurs to further camouflage the seam or interface. Two techniques developed by the present inventors for minimizing or eliminating unprinted seams are a roll-and-print technique and a differential stretch technique.

Figure 5A:
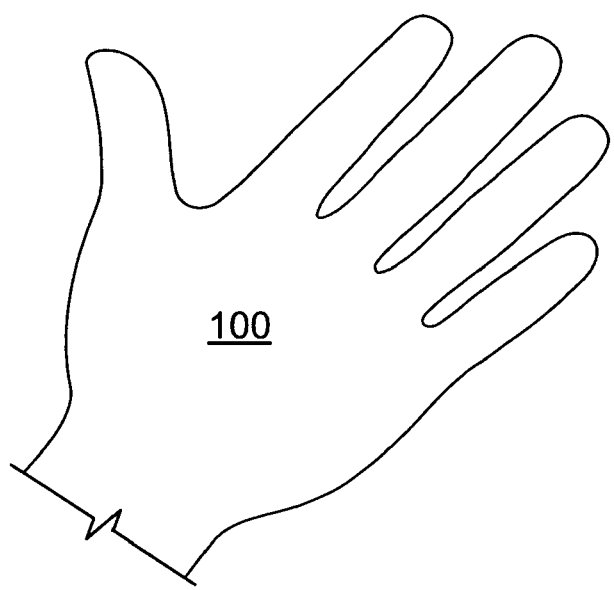
FIGS. 5A-5E are representations of the roll-and-print technique for minimizing or eliminating unprinted seams, as described below.
Figure 5B:
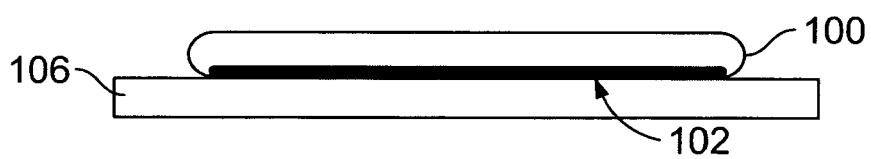
Figure 5C:
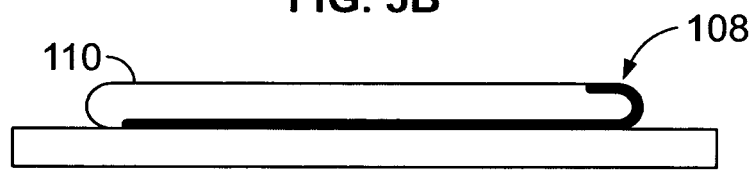
Figure 5D:
Figure 5E:
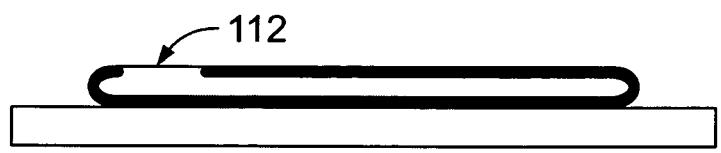

The roll-and-print technique is illustrated in FIGS. 5A-5E. FIG. 5A shows a top view of an elastic prosthesis such as a glove 100 which has a first representation 102 already printed in a first step on its bottom surface 104. An end view of glove 100 is represented diagrammatically in FIG. 5B in which first representation 102 is shown in exaggerated form by a heavy black line. Cover 100 is shown in this figure resting on a transport form 106. In the second step of this process, cover 100 is rolled to the left on the transport from which moves a portion 108 of representation 102 onto the exposed top surface 110 of the cover as shown in FIG. 5C. A second representation is then applied to the exposed top surface of the cover to extend the image coverage to all but a narrow unprinted band 112 of the cover. Finally, the cover is rolled to the right to move unprinted band 112 onto the exposed top surface of the cover and the appropriate portion of the representation is printed onto the unprinted band achieving full coverage of the cover. It should be noted that the extent of the roll to right and left and hence the width of the unprinted bands have been exaggerated for purposes of illustration. The thickness of the printed representation has also been exaggerated for purposes of illustration. Lastly, in a preferred embodiment multiple printed areas will receive representations of reduced opacity.

Figure 6A:
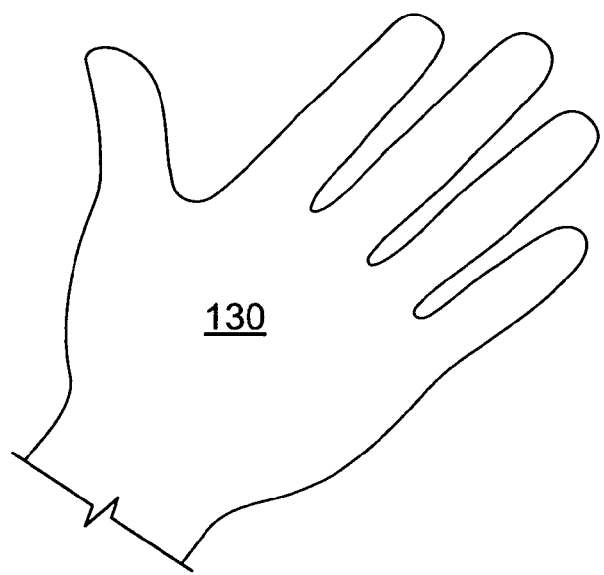
FIGS. 6A-6E are representations of the differential stretch technique for minimizing or eliminating unprinted seams, as described below.
Figure 6B:
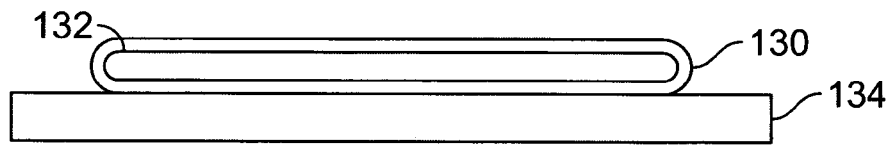
Figure 6C:
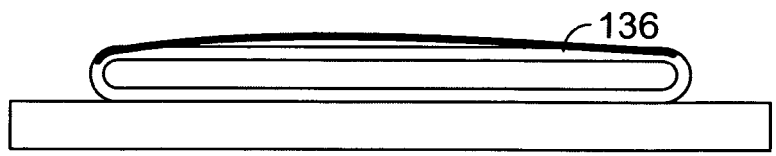
Figure 6D:
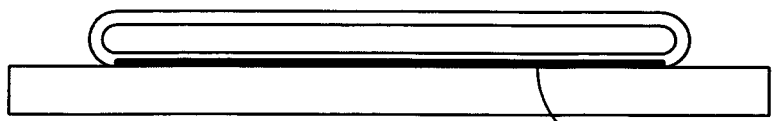
Figure 6E:
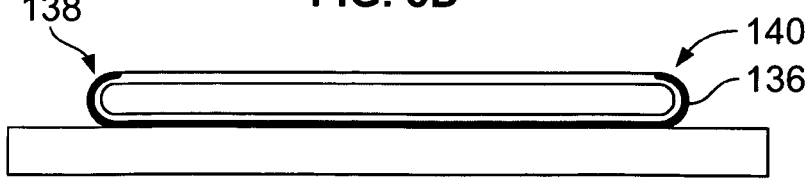

The differential stretch technique is illustrated in FIGS. 6A-6E. In this technique an elastic prosthesis cover such as glove 130 as shown in FIG. 6A with an expandable base 132 inside is positioned on a transport form 134. An end view of glove 130 is represented diagrammatically in FIG. 6B. A first representation 136 is shown in an exaggerated fashion by a heavy line applied to the top surface of the glove as shown in FIG. 6C. Next, the glove is flipped over so that the first representation is on the bottom of the glove resting on transport form 134 (FIG. 6D). Then the glove is expanded along its bottom side relative to the top side of the glove so that first representation 136 moves up past the edges of the glove into bands 138 and 140. At this point, a second representation is printed onto the top exposed surface of the glove which overlaps bands 138 and 140 thereby camouflaging the seam or interface of the top and bottom representations.

As previously discussed, in one embodiment the base cover material may be a heat-shrinkable material. The image is expanded for printing in a size such that the image will shrink to 100% upon final shrink-fitting to the target object (e.g., the prosthetic limb). When a heat-shrinkable material is used for the base cover, then the base cover may also be placed on a transport form and carriers for printing as described in the previous example, except that the base cover is not stretched during the process.

After the two-dimensional representation has been printed on the cover, the resulting product may be treated to improve wear and appearance, depending on the type of ink and material used for the base cover. For example, a waterproof coating and/or a gloss-reduction finish coating may be applied to provide the cover with a more realistic appearance as compared to latex or vinyl, which can otherwise have an unrealistic sheen. Coatings may be applied in a separate suitable application step such as with a spray or roller. Also, various portions of the cover can be treated with coatings that reduce both the gloss and surface friction, thereby making it easier for the amputee to put clothes over the cover according to various embodiments of the present invention.

Figure 7:
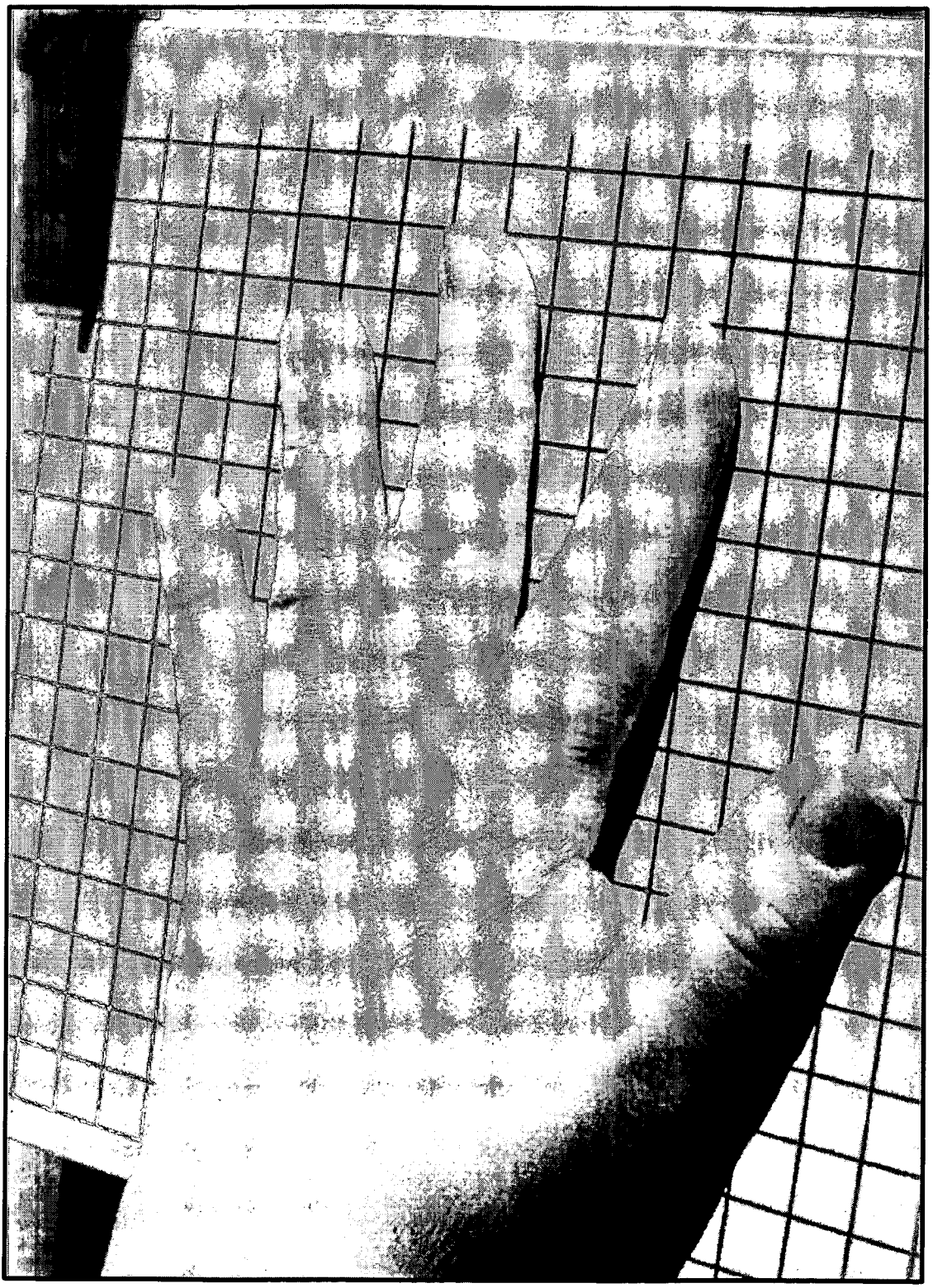
FIGS. 7-9 are digital photographs of a person's hand taken to produce an image in accordance with embodiments of the invention for application to a flexible cover.
Figure 8:
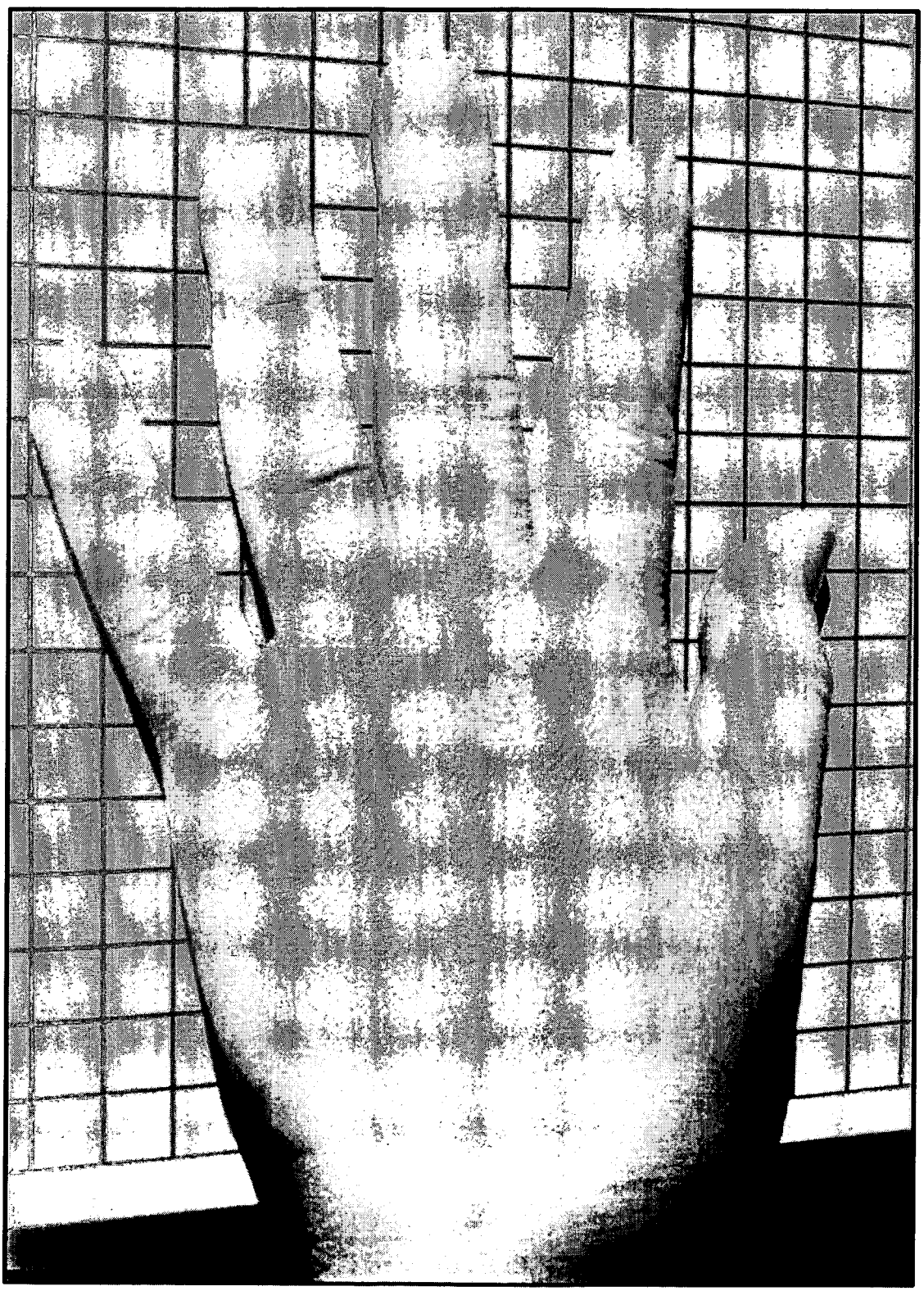
Figure 9:
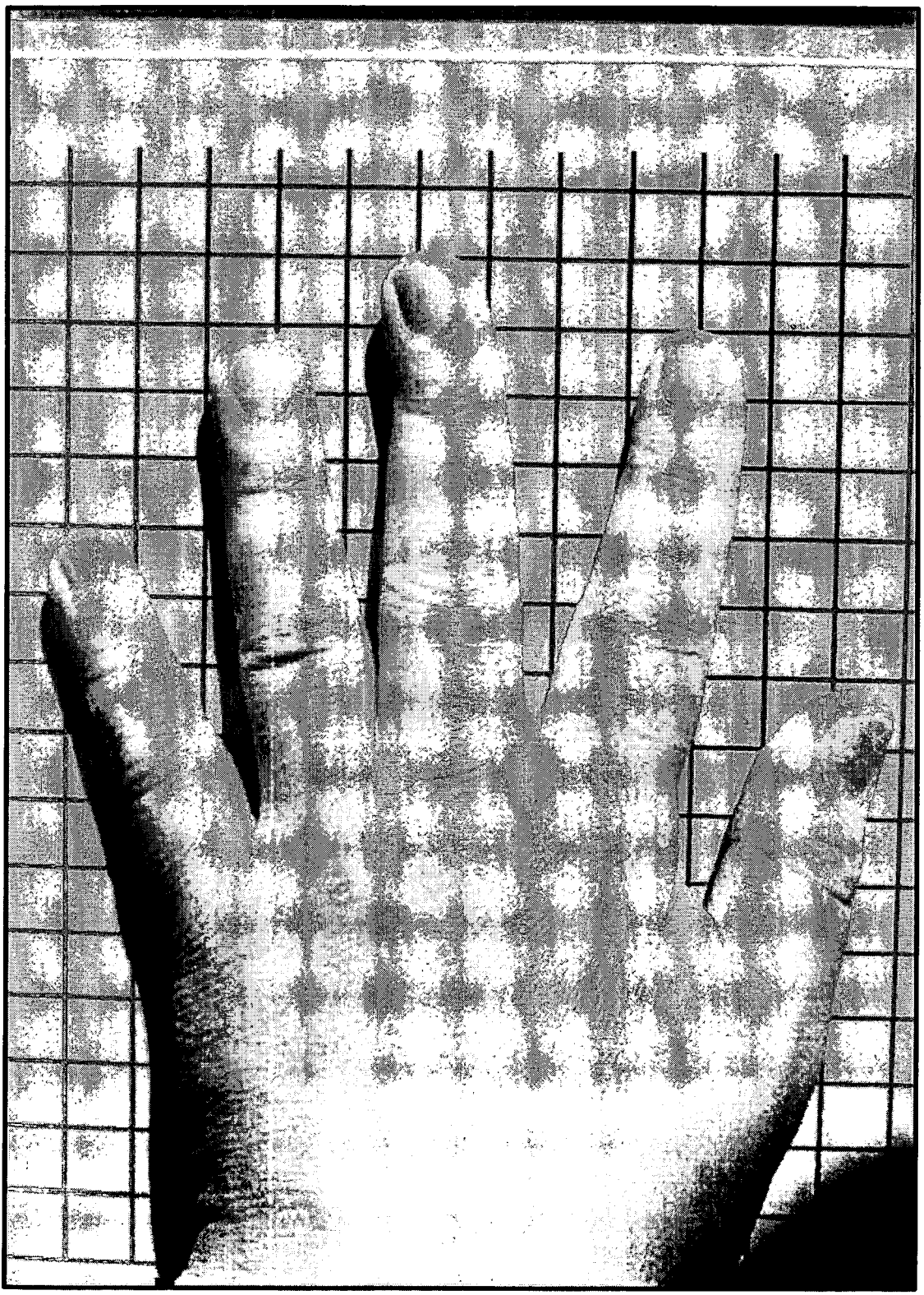

FIGS. 7-9 illustrate selected aspects of a method of making a hand prosthesis cover in accordance with embodiments of the invention. Thus, digital photographs are taken of a person's hand (the source object) from three different angles to produce the photographs of FIGS. 7, 8, and 9. These photographs were taken without the benefit of the use of the light chambers described above which would produce more even lighting and superior images.

Figure 10:
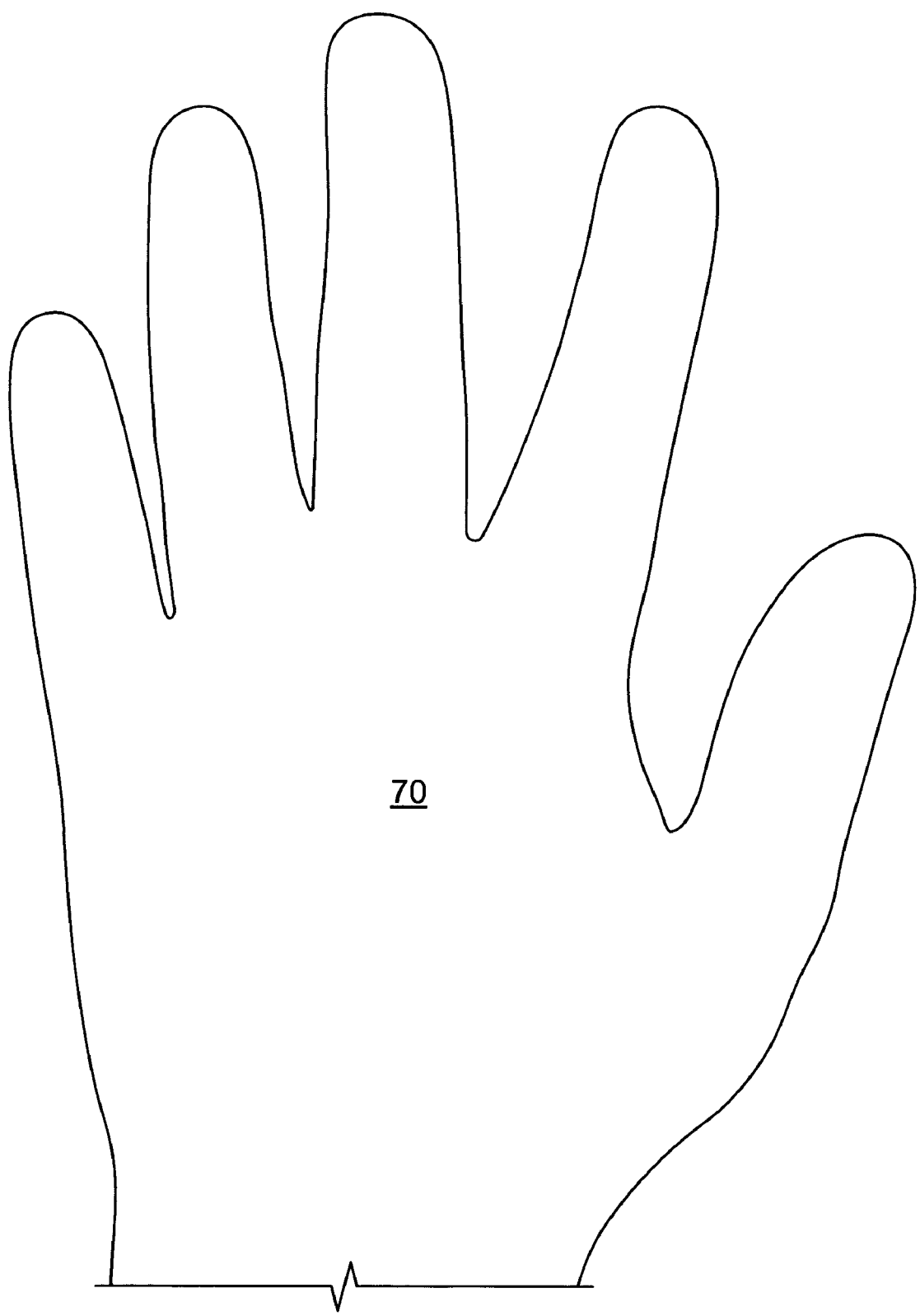
FIG. 10 is a photograph showing the relative sizes of a stretched glove and a person's hand serving as the source object.
Figure 11:
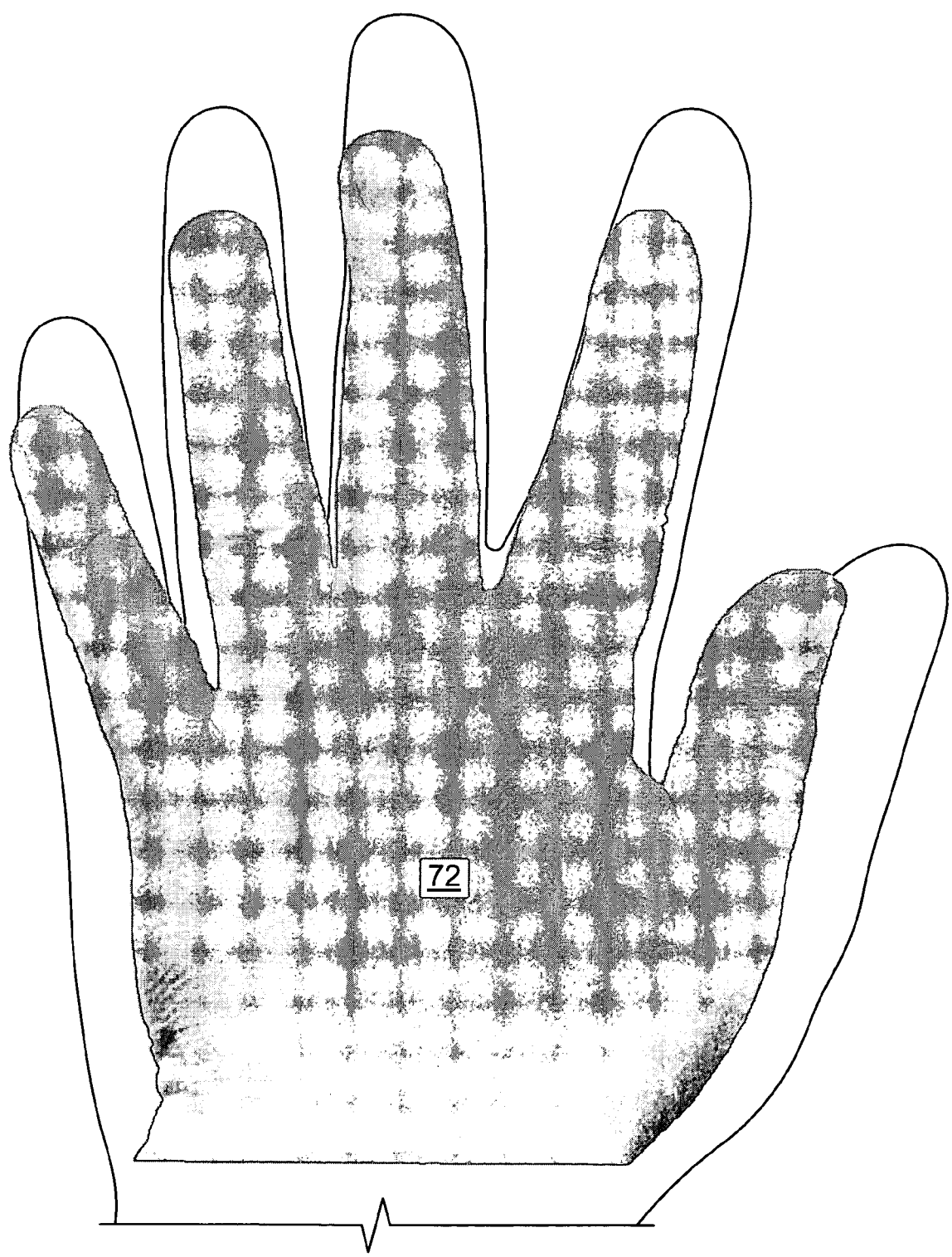
FIG. 11 shows the end product glove produced from the photographs of FIGS. 7-9.
Figure 12:
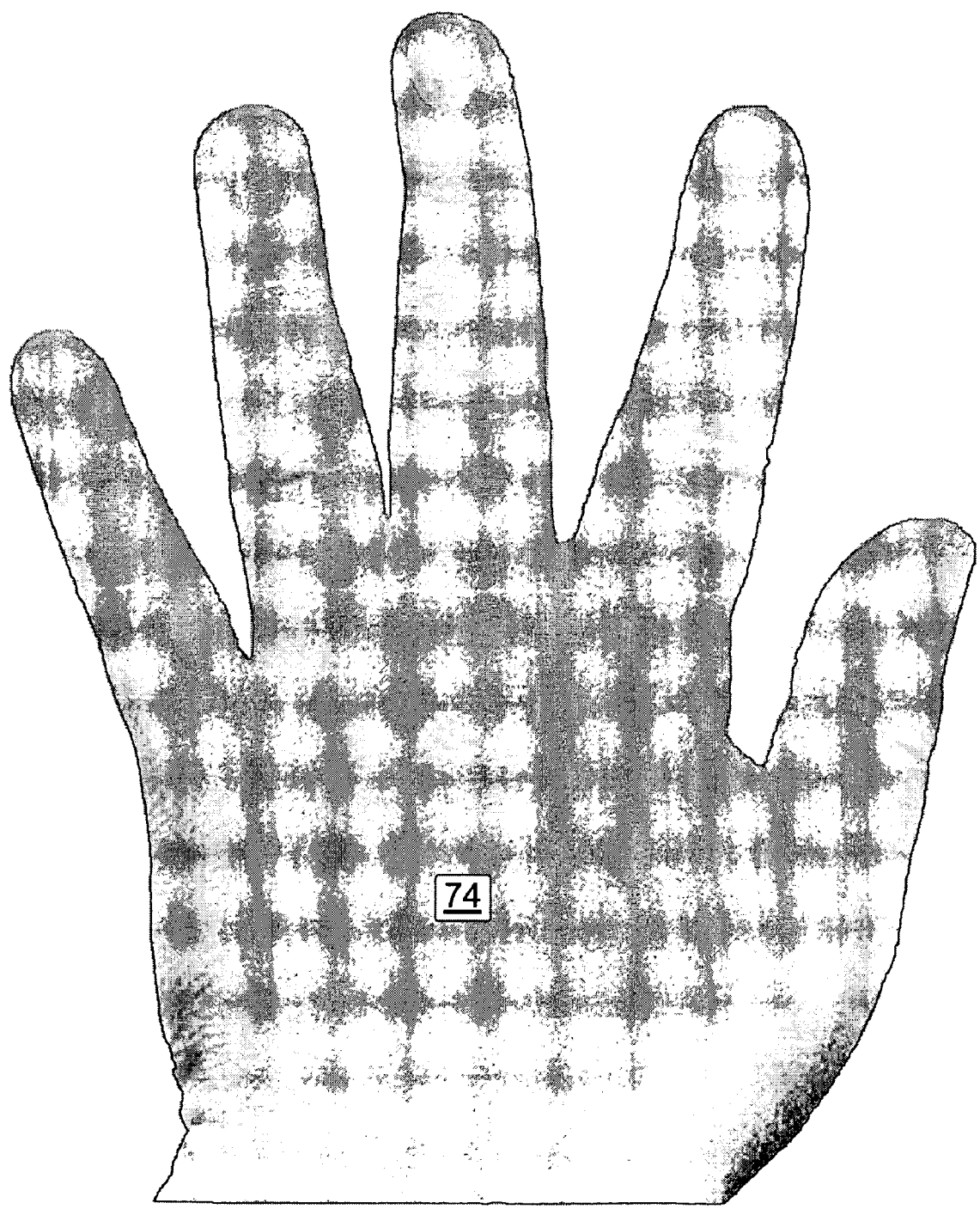
FIG. 12 shows the end product glove fitted over the target object.

Next, a nitrile rubber glove 70 is mounted onto an enlarged form to stretch the glove to a size about 110% of its nominal size as shown in the diagrammatic glove back view of FIG. 10. The relative sizes of the stretched glove 70 and the person's hand 72 serving as the source object shown in FIG. 11. Finally, FIG. 12 shows the end product 74, the back of a hand cover obtained by stitching together the digital images derived from the three photographs (FIGS. 7-9) corresponding to the source object. In the photograph of FIG. 12, the front of the glove has also been printed and the glove is fitted over the target object (the hand prosthesis) to demonstrate the realism anticipated in the end product.

Choosing Cover Color Profiles for Amputees

Although prosthesis covers made in accordance with embodiments of the invention will be substantially less expensive than artist painted prostheses (and more accurate), they still will involve significant expense. A person that receives a particular color cover and is unhappy with it, requiring that a different color cover be made, will incur substantial additional expense for a new cover. Misunderstandings will be able to be prevented by preparing a two-dimensional photograph of the skin tone or color chosen, so that the person will be able to be shown that the cover produced corresponds to the color chosen. The higher probability of the desired outcome achieved by previewing different colors and making a choice before the cover is made constitutes an important contribution of the present invention. Additionally, where color changes are desired, it will be possible to adjust the color without taking additional photographs by making appropriate adjustments in the data processed by the software as discussed above.

For Caucasians particularly, there are color changes in exposed limbs that occur due to season changes. That is, limbs that are exposed to the sun in the summer become suntanned or otherwise change in color due to sun exposure. The present invention makes it possible to adjust the image color to take into account the level of suntan where desired. Thus, in some cases, a person may have a "summer cover" and a "winter cover."

It can be seen from the foregoing that a new and useful method for making a cosmetic covering for prosthesis has been described. It should be noted that the use of the terms "a" and "an" and "the" and similar referents in the context of describing the invention (especially in the context of the following claims) are to be construed to cover both the singular and the plural, unless otherwise indicated. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

We claim:

1. A method for making a cover for a target object consisting of a prosthetic or orthotic device or other dynamic or flexible supporting member comprising:
   (a) capturing digital images of a source object;
   (b) digitally processing and manipulating the images to produce a representation of the surface of the source object; and
   (c) printing the representation of the surface onto a flexible cover configured to be applied to the target object wherein the flexible cover is transparent, and the image is printed on the inside of the flexible cover.

2. The method of claim 1 in which the source object is an exposed tubular limb structure.

3. The method of claim 2 in which the tubular limb structure is chosen from the group consisting of: hands, hands and arms up to the elbow, hands and arms up to the shoulder, fingers, feet, feet and ankles, feet and legs up to the knee, feet and legs up to the hip, tubular sections of arms, tubular sections of legs, the neck, and the trunk of the body.

4. The method of claim 1 in which the target object is chosen from the group consisting of hand, arm and leg prostheses.

5. The method of claim 1 in which the target object is chosen from the group consisting of leg braces, arm braces, and other appliances used to support, align or improve the function of movable body parts.

6. The method of claim 1 in which the source object is a portion of a person's skin and the cover acts as a skin prosthesis to cover scarred or tattooed portions of a tubular limb structure.

7. The method of claim 1 in which the source object is a portion of a person's skin, a tattoo image is introduced into the representation of the surface, and the flexible cover is adapted to be applied to a tubular limb structure to simulate the appearance of an authentic tattoo.

8. The method of claim 6 in which the flexible cover is positioned over a tattoo on a hand, arm, foot, leg or trunk of a person.

9. The method of claim 1 in which the flexible cover is free of unprinted seams.

10. The method of claim 1 in which the flexible cover is made of an elastic material.

11. The method of claim 1 in which the flexible cover is made of a heat-shrinkable material that shrinks at a uniform rate.

12. The method of claim 10 in which the elastic material is chosen from the group consisting of latex, silicone, rubber and vinyl.

13. The method of claim 12 in which the elastic material is nitrile rubber.

14. The method of claim 10 in which the elastic material has an ink receptor coating.

15. The method of claim 1 in which the flexible cover comprises two or more abutting parts that are free to move with respect to each other, the two or more abutting parts bearing a consistent image across the parts.

16. The method of claim 15 in which the two or more abutting parts overlap.

17. The method of claim 15 in which two or more of the parts are made of materials having different wear characteristics or thicknesses.

18. The method of claim 15 in which the flexible cover is in the shape of a glove including abutting wrist and arm portions.

19. The method of claim 10 in which the elastic material can be stretched without damage to at least about 20% of its nominal size.

20. The method of claim 10 in which the elastic material can be stretched without damage to at least about 10% of its nominal size.

21. The method of claim 10 in which the flexible cover is made from material having a thickness from about 0.003 to about 0.050 inches.

22. The method of claim 10 in which the flexible cover is made from material having a thickness from about 0.008 to about 0.012 inches.

23. The method of claim 1 in which the flexible cover includes an inner cover portion physically textured to emulate the source object and in which the cover further includes a generally smooth outer cover portion.

24. The method of claim 1 in which selected areas of the flexible cover are provided with enhanced friction surfaces.

25. The method of claim 1 further comprising creating a custom color profile for each flexible cover base color and material type and employing the custom color profile in adjusting the color of the representation of the surface printed onto the flexible cover.

26. The method of claim 25 in which the custom color profiles are created by printing known color values on different colors and types of cover material, allowing the printed known color values to stabilize, measuring resulting colors and characteristics, and adjusting ink color ratios through incremental testing until desired calibrated target characteristics are achieved.

27. The method of claim 1 in which the digital images of the source object are captured using a chamber fitted for shadowlessly lighting the source object while photographing the source object from spaced angles to produce overlapping photographs.

28. The method of claim 27 in which the photographs overlap by at least about 10%.

29. The method of claim 27 in which the photographs overlap by at least about 30%.

30. The method of claim 1 in which the digital images are stitched together and adjusted to achieve a desired color, and resized as necessary to accommodate expansion or contraction of the flexible cover when the flexible cover is fitted onto a prosthetic device, an orthotic device, or a dynamic or flexible supporting member.

31. The method of claim 1 in which the target object is a prosthetic or orthotic device and the method further includes editing to remove scars or anomalies before applying the representation to the cover.

32. The method of claim 1 in which the target object is a prosthetic or orthotic device and the method further includes adjusting the color of the representation to account for changes in skin color due to the acquisition or loss of sun tan or due to other temporal changes in skin pigmentation in a limb that serves as the source object.

33. The method of claim 1 in which the target object is a prosthetic or orthotic device and the method includes capturing digital images of varying skin colors in a limb that is to serve as the source object.

34. The method of claim 33 in which the digital images of varying skin colors are captured by photographing the limb that serves as the source object while the limb is at varying positions in space.

35. The method of claim 33 in which the digital images of varying skin colors are obtained by photographing the limb that serves as the source object while the limb is maintained in environments at varying temperatures.

36. The method of claim 1 in which the target object is a robotic arm.

37. The method of claim 1 in which the target object is a dynamic or flexible device that is not a body part.

38. The method of claim 1 further comprising positioning the cover on a substantially flat transport form and transporting the form through a printer to print onto one side of the flexible cover.

39. The method of claim 38 further comprising flipping the transport form and again transporting the form through the printer to print onto the opposite side of the flexible cover.

40. The method of claim 1 in which the flexible cover is maintained generally flat while the representation is printed.

41. The method of claim 1 in which the surface of the flexible cover is textured.

42. A method for making a flexible cover for dynamic or flexible prosthetic or orthotic devices comprising:
   (a) creating enhanced lighting conditions;
   (b) arranging one or more cameras to photograph from at least two different vantage points a three-dimensional source object comprising a body part or a body surface whose appearance is to be replicated on the prosthetic or orthotic device;
   (c) capturing digital images of the source object with one or more cameras;
   (d) digitally processing and manipulating the digital images to produce a representation of the surface of the source object; and
   (e) printing the representation of the surface onto a flexible cover configured to fit over and follow contours of the prosthetic or orthotic device wherein the flexible cover is transparent, and the image is printed on the inside of the flexible cover.

43. A method for making a cover for a target object consisting of a prosthetic or orthotic device or tubular limb structure comprising:
   (a) capturing sets of digital images of the surface of a limb of a person where the sets display varying skin colors;
   (b) displaying digital images selected from each set to a person requiring a cover for a prosthetic or orthotic device to enable the person to select a preferred set of images;
   (c) digitally processing and manipulating the digital images of a selected set to produce a representation of the surface of the limb; and
   (d) printing the representation onto a flexible cover configured to be applied to the target object wherein the flexible cover is transparent, and the image is printed on the inside of the flexible cover.

44. The method of claim 1 in which the digital images of the source object are captured using a lighting source arranged for shadowlessly lighting the source object while photographing the source object from spaced angles to produce overlapping photographs.

45. The method of claim 1 in which the digital images are stitched together and adjusted to achieve a desired color, and resized as necessary to accommodate expansion or contraction of the flexible cover when the flexible cover is fitted onto a portion of a person's skin to act as a skin prosthesis to cover scarred or tattooed portions of a tubular limb structure.

46. The method of claim 1 in which the target object is a portion of a person's skin and the method further includes adjusting the color of the representation to account for changes in skin color due to the acquisition or loss of sun tan or due to other temporal changes in skin pigmentation.

47. The method of claim 1 in which the target object is a portion of a person's skin and the method includes capturing digital images of varying skin colors in a limb that is to serve as the source object.

48. The method of claim 1 in which the target object is a portion of a person's skin.

* * * * *